United States Patent [19]
Ouellette et al.

[11] Patent Number: 5,741,318
[45] Date of Patent: Apr. 21, 1998

[54] ELASTIC BACK WRAP HAVING DIAMOND-SHAPED THERMAL PATTERN AND ANTI-SLIP MEANS

[75] Inventors: William R. Ouellette, Cincinnati, Ohio; Sandra H. Clear, Longwood, Fla.; Kurt E. Holstein, Cincinnati, Ohio; Elizabeth M. Harvey; Timothy A. Burkett, both of West Chester, Ohio; Jean Mallett, Lebanon, Ohio

[73] Assignee: The Procter & Gamble Company, Cincinnati, Ohio

[21] Appl. No.: 686,800

[22] Filed: Jul. 26, 1996

Related U.S. Application Data

[63] Continuation of Ser. No. 496,373, Jun. 29, 1995.
[51] Int. Cl.6 ...................................................... A61F 7/10
[52] U.S. Cl. ........................ 607/108; 607/112; 607/114; 165/46
[58] Field of Search ............................ 607/96, 98, 104, 607/108–114; 602/1–12, 17–27; 600/9–15; 219/211, 528; 62/530; 165/46; 2/311, 312, 337

[56] References Cited

U.S. PATENT DOCUMENTS

| 3,149,943 | 9/1964 | Amador | 62/4 |
|---|---|---|---|
| 3,667,462 | 6/1972 | Moor | 128/169 |
| 3,736,769 | 6/1973 | Peterson | 62/530 |

(List continued on next page.)

FOREIGN PATENT DOCUMENTS

| 0 014 300 A1 | 8/1980 | European Pat. Off. . | |
|---|---|---|---|
| 0 324 578 A1 | 7/1989 | European Pat. Off. . | |
| 0 370 600 A1 | 5/1990 | European Pat. Off. . | |
| 160433 SHO | 7/1987 | India | C09K 3/02 |
| 58-132074 | 8/1983 | Japan | C09K 5/00 |
| Hei 6-241575 | 8/1994 | Japan | F24J 1/02 |
| Hei 7-124192 | 5/1995 | Japan | A61F 7/08 |
| Hei 7-194642 | 8/1995 | Japan | A61F 7/08 |
| 2 205 496 | 1/1988 | United Kingdom . | |
| 2 205 496 | 12/1988 | United Kingdom . | |
| 2255722 | 11/1992 | United Kingdom | 600/15 |
| WO 94/00087 | 1/1994 | WIPO . | |
| WO 94/12125 | 6/1994 | WIPO . | |

OTHER PUBLICATIONS

U.S. application No. 08/496,565, Ouellette et al., filed Jun. 19, 1995.

(List continued on next page.)

*Primary Examiner*—John P. Lacyk
*Assistant Examiner*—David M. Ruddy
*Attorney, Agent, or Firm*—Ronald W. Kock

[57] ABSTRACT

A substantially rectangular piece of flexible web having a first end and a second end and an elastic portion therebetween, stretchable along a longitudinal axis of the piece of web. The piece of web has a length great enough to encircle a user's waist such that the first and second ends overlap. The first end has a reclosable fastening system for attaching the first end to the piece of web near the second end in order to hold the piece of web around the user's waist when the piece of web is stretched. The back wrap further comprises a plurality of individual thermal elements embedded in the piece of web. The plurality of thermal elements have a substantially planar diamond-shaped pattern which approximates the shape of erector muscles in the user's back. The pattern has a gap transverse to the longitudinal axis which corresponds to the user's spine. The elastic back wrap may further include an individual thermal element located in the gap of the pattern such that the single thermal element covers the user's sacroiliac at the base of the user's spine. The elastic back wrap has a means for increasing friction between the piece of web and a user's body in order to reduce slippage of the wrap during use. The means for increasing friction may include a foam strip attached transverse to the longitudinal axis of the piece of web on the body-facing side thereof.

1 Claim, 2 Drawing Sheets

U.S. PATENT DOCUMENTS

| | | | |
|---|---|---|---|
| 3,882,867 | 5/1975 | Moran | 128/254 |
| 3,893,460 | 7/1975 | Karami | 128/287 |
| 3,900,035 | 8/1975 | Welch et al. | 128/402 |
| 3,943,912 | 3/1976 | Nakayama | 600/15 |
| 3,955,575 | 5/1976 | Okuda | 128/284 |
| 3,976,049 | 8/1976 | Yamashita et al. | 126/263 |
| 4,044,773 | 8/1977 | Baldwin, III | 128/402 |
| 4,081,150 | 3/1978 | Tyson | 128/402 |
| 4,190,054 | 2/1980 | Brennan | 128/402 |
| 4,204,543 | 5/1980 | Henderson | 128/402 |
| 4,243,041 | 1/1981 | Paul | 128/402 |
| 4,255,157 | 3/1981 | Yamaguchi et al. | 44/3 C |
| 4,268,272 | 5/1981 | Taura | 44/3 R |
| 4,282,005 | 8/1981 | Sato et al. | 44/3 R |
| 4,366,804 | 1/1983 | Abe | 126/263 |
| 4,516,564 | 5/1985 | Koiso et al. | 126/263 |
| 4,527,566 | 7/1985 | Abare | 128/402 |
| 4,575,097 | 3/1986 | Brannigan et al. | 128/402 |
| 4,586,506 | 5/1986 | Nangle | 128/403 |
| 4,628,918 | 12/1986 | Johnson, Jr. | 128/90 |
| 4,628,932 | 12/1986 | Tampa | 128/402 |
| 4,669,476 | 6/1987 | Gordon et al. | 128/399 |
| 4,671,267 | 6/1987 | Stout | 128/156 |
| 4,706,658 | 11/1987 | Cronin | 128/77 |
| 4,756,299 | 7/1988 | Podella | 126/263 |
| 4,802,667 | 2/1989 | Altner | 272/123 |
| 4,805,620 | 2/1989 | Meistrell | 128/402 |
| 4,860,748 | 8/1989 | Chiurco et al. | 128/399 |
| 4,886,063 | 12/1989 | Crews | 128/403 |
| 4,891,501 | 1/1990 | Lipton | 219/527 |
| 4,914,717 | 4/1990 | Gibbon | 219/10.55 M |
| 4,925,743 | 5/1990 | Ikeda et al. | 428/702 |
| 4,961,418 | 10/1990 | McLaurin-Smith | 128/157 |
| 4,972,832 | 11/1990 | Trapini et al. | 128/402 |
| 4,981,135 | 1/1991 | Hardy | 128/402 |
| 5,000,176 | 3/1991 | Daniel | 128/402 |
| 5,007,416 | 4/1991 | Burns et al. | 128/80 H |
| 5,027,801 | 7/1991 | Grim | 128/80 H |
| 5,046,479 | 9/1991 | Usui | 126/204 |
| 5,062,269 | 11/1991 | Siegel | 62/4 |
| 5,062,414 | 11/1991 | Grim | 607/108 |
| 5,065,758 | 11/1991 | Whitehead et al. | 128/402 |
| 5,072,598 | 12/1991 | Dibrell | 62/259.3 |
| 5,086,629 | 2/1992 | Dibrell | 62/259.3 |
| 5,086,761 | 2/1992 | Ingram | 602/26 |
| 5,088,487 | 2/1992 | Turner | 128/402 |
| 5,088,549 | 2/1992 | Schneider | 165/46 |
| 5,094,238 | 3/1992 | Gibbon | 128/403 |
| 5,133,348 | 7/1992 | Mayn | 128/403 |
| 5,165,402 | 11/1992 | McCoy | 128/402 |
| 5,179,942 | 1/1993 | Drulias et al. | 607/108 |
| 5,179,944 | 1/1993 | McSymytz | 128/403 |
| 5,190,033 | 3/1993 | Johnson | 128/403 |
| 5,211,623 | 5/1993 | Sarkozi | 602/18 |
| 5,233,981 | 8/1993 | Miyashita et al. | 607/114 |
| 5,269,023 | 12/1993 | Ross | 2/66 |
| 5,342,412 | 8/1994 | Ueki | 607/114 |
| 5,366,491 | 11/1994 | Ingram et al. | 607/108 |
| 5,373,582 | 12/1994 | Dragone et al. | 2/2.5 |
| 5,375,261 | 12/1994 | Lipke | 2/92 |
| 5,378,225 | 1/1995 | Chatman, Jr. | 602/19 |
| 5,398,667 | 3/1995 | Witt | 126/263 |
| 5,399,130 | 3/1995 | Saunders | 602/19 |
| 5,450,858 | 9/1995 | Zablotsky et al. | 600/15 |
| 5,451,201 | 9/1995 | Prengler | 602/26 |
| 5,496,357 | 3/1996 | Jensen et al. | 607/108 |
| 5,500,959 | 3/1996 | Yewer, Jr. | 602/19 |
| 5,534,021 | 7/1996 | Dvoretzkky et al. | 607/112 |

OTHER PUBLICATIONS

U.S. application No. 08/496,716, Burkett et al., filed Jun. 29, 1995.

U.S. application No. 08/496,594, Ouellette, filed Jun. 29, 1995.

U.S. application No. 08/496,373, Ouellette et al., filed Jun. 29, 1995.

U.S. application No. 08/496,639, Burkett et al., filed Jun. 29, 1995.

U.S. application No. 08/604,694, Burkett et al., filed Feb. 21, 1996.

U.S. application No. 29/040,849, Davis et al., filed Jun. 29, 1995.

U.S. application No. 08/672,166, Viltro et al., filed Jun. 27, 1996.

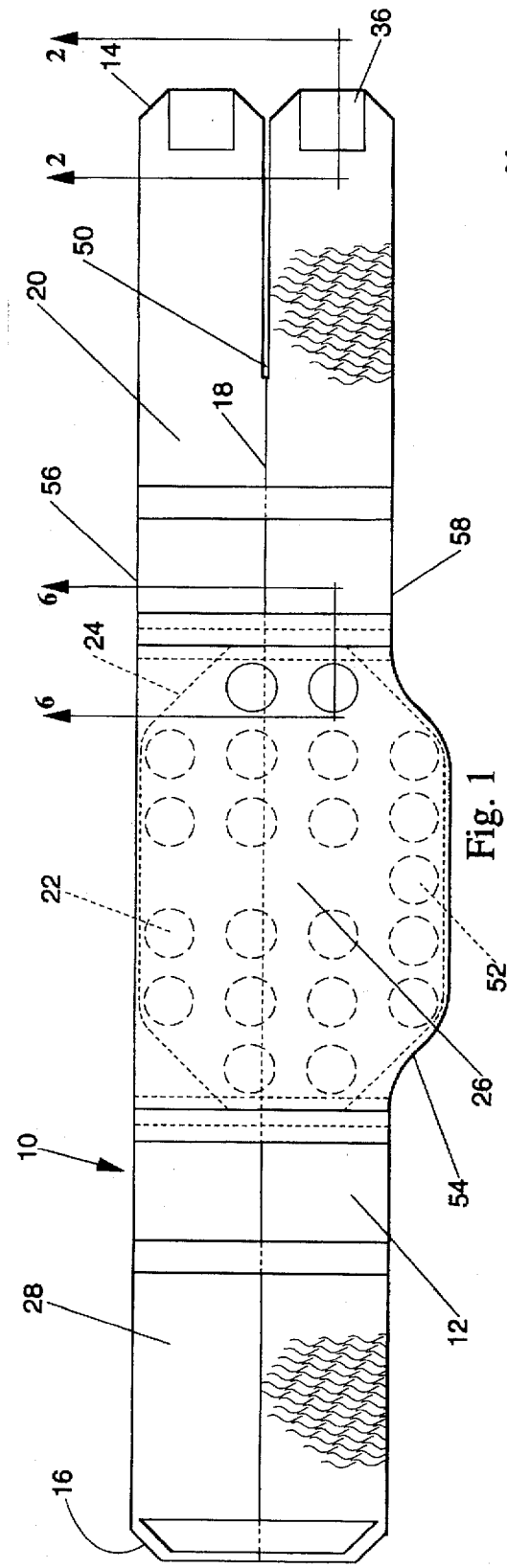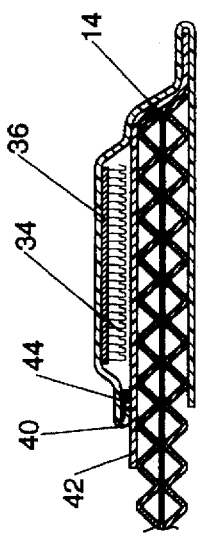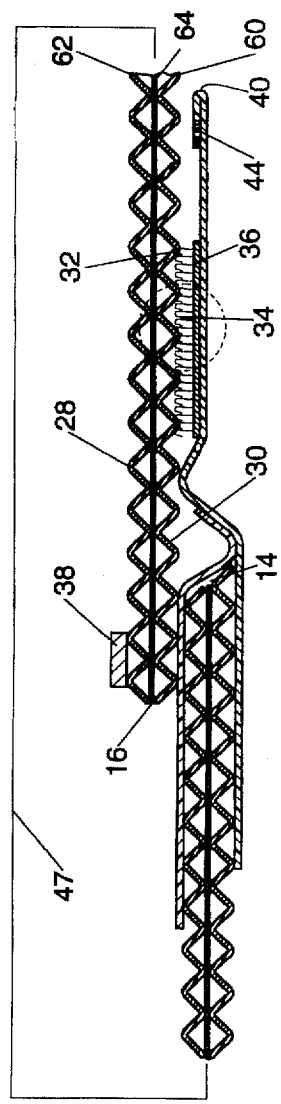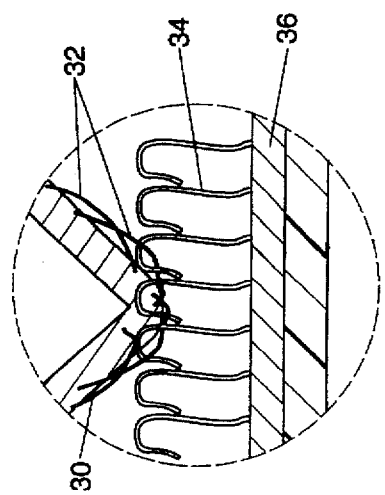
Fig. 1
Fig. 2
Fig. 3A
Fig. 3B

ELASTIC BACK WRAP HAVING DIAMOND-SHAPED THERMAL PATTERN AND ANTI-SLIP MEANS

This is a continuation of application Ser. No. 08/496,373, filed on Jun. 29, 1995.

FIELD OF THE INVENTION

The present invention relates to back wraps having thermal elements for temporary pain relief application, and more particularly to back wraps wherein the thermal energy is applied to specific areas of the lower back. Even more particularly, the present invention relates to elastic back wraps having features to position and maintain thermal elements in the desired location during use.

BACKGROUND OF THE INVENTION

Chronic back pain is one of the most common complaints found in modern society. Heating pads and elastic compression bands are common devices used to relieve chronic back pain. More recently, combinations of elastic back wraps and heating pads have been available. Many of these combination devices utilize thermal packs which are reusable via the replenishment of thermal energy including heated water and microwaveable gels. In general, however, the state of the art is rather archaic. Such temporary pain relief devices are inconvenient to use on a regular basis because: thermal energy is not immediately available when needed; thermal energy is not released in a controllable or sustainable manner; positioning of thermal energy elements for heating only the back muscles, rather than the spine or other areas which do not benefit as much from thermal treatment, is inaccurate and difficult to maintain; or adjustability for waist size and tension comfort has been missing.

What is needed is an inexpensive disposable back wrap which provides instant heating in a controlled and sustainable manner, wrap alignment and position maintenance features, a fastening system which a wide variety of users can easily manipulate to achieve tension comfort, and a thermal element pattern which directs thermal energy to where it has the most temporary pain relief benefit.

SUMMARY OF THE INVENTION

In one aspect of the present invention an elastic back wrap comprises a substantially rectangular piece of flexible web having a first end and a second end and an elastic portion therebetween stretchable along a longitudinal axis of the piece of flexible web. The piece of flexible web has a length great enough to encircle a user's waist such that the first and second ends overlap. The first end has a reclosable fastening system for attaching the first end to the piece of flexible web near the second end in order to hold the piece of flexible web around the user's waist when the piece of flexible web is stretched. The back wrap further comprises a plurality of individual thermal elements embedded in the piece of flexible web. The plurality of thermal elements have a substantially planar diamond-shaped pattern which approximates the shape of erector muscles in the user's back. The pattern has a gap transverse to the longitudinal axis which corresponds to the user's spine. The elastic back wrap may further comprise an individual thermal element located in the gap such that the thermal element covers the users sacroiliac at the base of the user's spine.

The fastening system has a plurality of hook members which engage loop fibers of the piece of flexible web anywhere along the piece of web in order to adjust the wrap to a variety of user waist sizes and to attain a comfortable level of elastic tension. The piece of web has a continuous outer surface which is either a knitted material, brushed to increase nap and thereby expose a plurality of loop fibers, or a nonwoven material which is puckered to generate a plurality of loop fibers.

The elastic back wrap may further comprise a means for increasing friction between the piece of flexible web and a user's body in order to reduce slippage of the wrap during use. The piece of flexible web has a body-facing side. The means for increasing friction may include a foamed polymer strip attached transverse to the longitudinal axis of the piece of flexible web on the body-facing side, or it my include a stripe of high-tack polymer printed transverse to the longitudinal axis of the piece of web on the body-facing side.

The elastic back wrap may have a slit through the fastening system and a portion of the piece of flexible web, the slit extending substantially parallel to the longitudinal axis of the piece of flexible web. The slit generates a plurality of independently fastenable first ends, providing better back wrap adjustability.

BRIEF DESCRIPTION OF THE DRAWINGS

While the specification concludes with claims which particularly point out and distinctly claim the present invention, it is believed that the present invention will be better understood from the following description of preferred embodiments, taken in conjunction with the accompanying drawings, in which like reference numerals identify identical elements and wherein:

FIG. 1 is a top plan view of a preferred embodiment of the elastic back wrap of the present invention, showing the preferred diamond-shaped pattern of thermal units therein;

FIG. 2 is a sectioned side elevation view thereof, taken along section line 2—2 of FIG. 1, disclosing a hook fastener connected to one end of the wrap and folded over against a release paper to prevent inadvertent engagement of the hooks with the wrap material;

FIG. 3A is a sectioned side elevation view thereof, similar to FIG. 2, disclosing the hook fastener end of the wrap overlapping and engaging another portion of the wrap, and an anti-slip strip attached to one end of the back wrap on the body-facing side;

FIG. 3B is an enlarged view of a portion of FIG. 3A, disclosing hooks engaged with loop fibers at rugosities of the elastic wrap material.

DETAILED DESCRIPTION OF THE INVENTION

Figure 4:
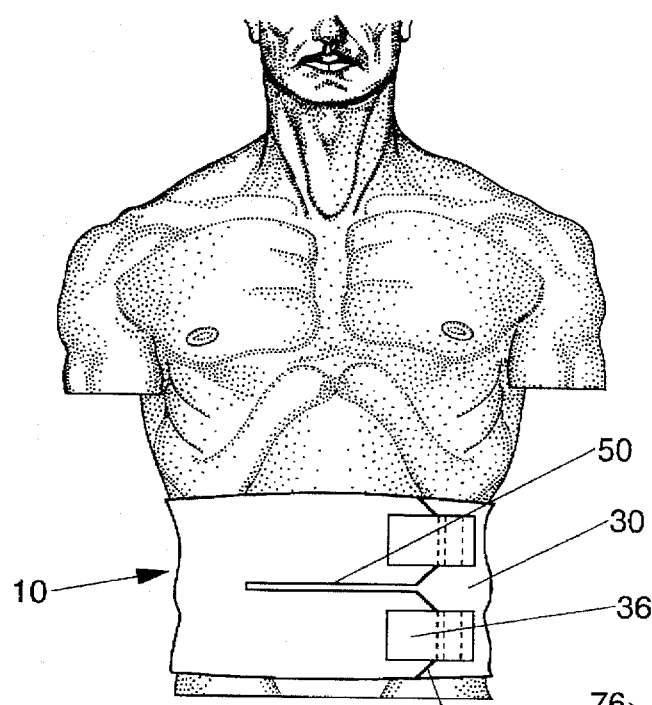
FIG. 4 a perspective view thereof, showing the back wrap applied to a user's back with the fastening portion at the user's front.
Figure 6:
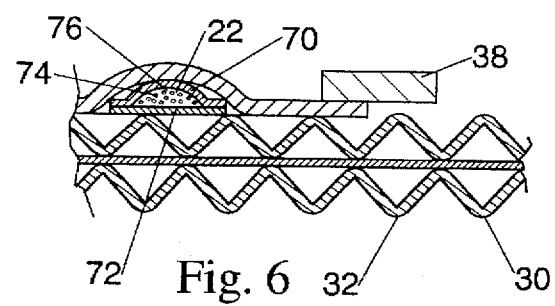
FIG. 6 is an enlarged sectioned side elevation thereof, taken along section line 6—6 of FIG. 1, disclosing a thermal cell embedded in the laminated material of the back wrap.
Figure 5:
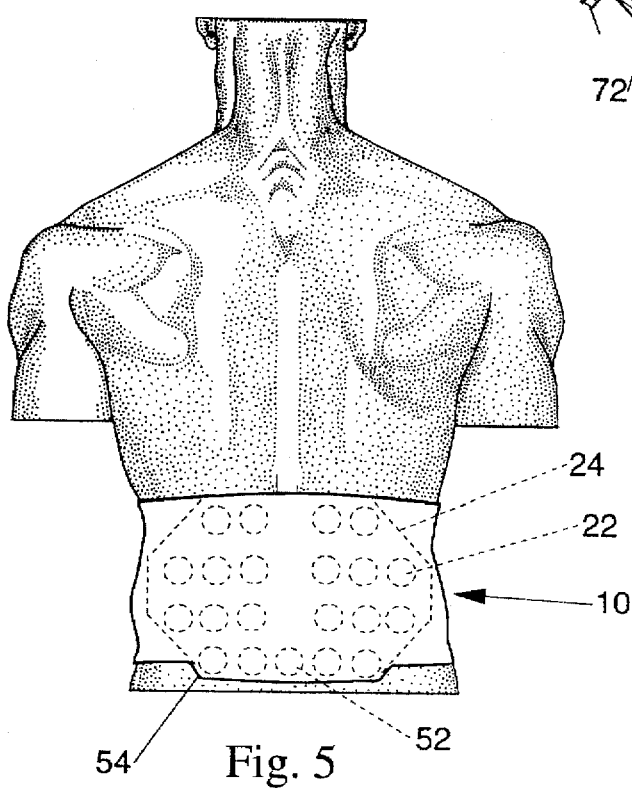
FIG. 5 is a perspective view thereof, showing the location of the back wrap and its thermal pattern relative to the muscles of the lower back.

Referring now to the drawings, and more particularly to FIGS. 1 and 2, there is shown a first preferred embodiment of the present invention, which provides an elastic back wrap and is generally indicated as 10. As used herein elastic refers to that property of a material whereby the material, when subjected to a tensile force, will stretch or expand in the direction of the force and will essentially return to its original untensioned dimension upon removal of the force. Elastic back wrap 10 is comprised of a substantially rectangular piece of flexible web 12 having a longitudinal axis 18. Flexible web 12 has a first end 14 and a second end 16 and an elastic portion 20 therebetween capable of being stretched along longitudinal axis 18. Flexible web 12 also has a first edge 56 and an opposing second edge 58, both first edge 56 and second edge 58 extending from first end 14 to second end 16. Flexible web 12 further has a length, as measured in a direction parallel to longitudinal axis 18, which is great enough to encircle a user's waist and allow first end 14 to overlap second end 16 when wrap 10 is stretched around a user. Flexible web 12 of back wrap 10 has a body-facing side 28 and a continuous outer surface 30, both body-facing side 28 and outer surface 30 extending from first end 14 to second end 16.

Preferably, outer surface 30 of wrap 10 contains a plurality of loop fibers 32 disposed along longitudinal axis 18. Plurality of loop fibers 32 serve as the loop member of a reclosable hook and loop fastening system. As used herein the term reclosable refers to that property of a fastening system which provides for initial closing of the fastening system, a subsequent opening of the fastening system, followed by at least one additional closings of the same fastening system. The subsequent closing of the fastening system may either return the closure to the original position or it may result in a repositioning of the closure from the initial configuration. Body-facing side 28 of web 12 contains a plurality of hooks 34 defining hook member 36 which is permanently connected to body-facing side 28 adjacent first end 14. As used herein, the term permanently connected is defined as the joining of two or more elements which remain joined during their intended use. Hook member 36 on body-facing side 28, together with plurality of loop fibers 32 on outer surface 30, provide a reclosable hook and loop fastening system for securing first end 14 of web 12 to outer surface 30 of web 12 to hold wrap 10 in position when flexible web 12 is stretched around the wearer's waist, such that first end 14 engages second end 16, as depicted in FIG. 3A. In FIG. 3A flexible web 12 is shown with first end 14 overlapping second end 16. This overlapping of web 12 positions hook member 36 on side 28 over loop fibers 32 of surface 30. Since loop fibers 32 are disposed continuously along longitudinal axis 18, hook member 36 may be engaged with loop fibers 32 at any position along continuous outer surface 30 of web 12.

Since hook member 36 is capable of engaging loop fibers 32 at any point along web 12, it is desired that hooks 34 be protected from engaging with loops 32 prior to application by the user. Preferably, hook member 36 is affixed to a grip tab 40, said grip tab 40 extending longitudinally beyond hook member 36 adjacent first end 14. Prior to use, grip tab 40, with hook member 36 attached is folded against and removably secured against a release paper 42 by a pressure sensitive adhesive strip 44 extending generally the width of grip tab 40 in a direction transverse to longitudinal axis 18 of web 12, as depicted in FIG. 2A. Release paper 42 remains attached to web 12 at first end 14 throughout application and use. Upon application the user positions wrap 10 and then removes grip tab 40, with hook member 36 attached thereto, from release paper 42. The removal of grip tab 40 from release paper 42 exposes hook member 36 which is then engaged with loop fibers 32 as depicted in FIG. 3B.

Hooks 34 may be any number of styles, shapes, and/or densities depending upon the use. Hooks 34 may be heat shafts as in FIG. 3B, mushroom capped, harpoon-shaped, or any other suitable shape. Hooks 34 may be unidirectional, bi-directional, or omni-directional depending upon the application and companion loop fibers 32. Hooks 34 must be chosen in conjunction with companion loop fibers 32 so as to provide the peel and shear forces that are required for different applications.

Preferably, piece of flexible web 12, hook member 36, and grip tab 40 have a slit 50 therethrough substantially parallel to longitudinal axis 18 staring at first end 14 and extending into web 12. Slit 50 provides a plurality of first ends 14 each containing its own hook member 36 which can be independently fastened to loop fibers 32. This arrangement allows easier application of the wrap to the user and differential tensioning of web 12 during use. Slit 50 is preferably about 180 mm long.

Elastic back wrap 10 also includes a plurality of individual thermal elements 22 arranged in a substantially planar diamond-shaped pattern, as indicated by dotted line 24, and a lower flap portion 54 extending outwardly from second edge 58. Thermal elements 22 are depicted in FIG. 1 extending into lower flap portion 54 which is intended to position thermal elements 22 low on the back of the user. Alternatively, lower flap portion 54 may be omitted and thermal elements 22 repositioned on wrap 10 so as to be contained entirely between first edge 56 and second edge 58. Preferably, the arrangement of individual thermal elements 22 includes a gap 26, which is oriented transverse to longitudinal axis 18 of flexible web 12. Gap 26 is intended to be placed over and correspond to the user's spine when the user wears back wrap 10. Preferably, the distance from gap 26 to first end 14 is larger than the distance from gap 26 to second end 16. In this way when gap 26 is positioned over the wearer's spine, the attachment of first end 14 to web 12 is shifted off-center of the wearer's front, as depicted in FIG. 4. This arrangement repositions the overlapped portion of wrap 10 to the wearer's side, reducing bulk in the center waist area. Shifting off-center also positions slit 50 over the wearer's abdomen. Slit 50 is then able to separate and allow flexible web 12 to more closely follow the anatomy of the wearer as the dimensions of the wearer's abdomen change during movement. Preferably, the arrangement of thermal elements 22 includes an additional thermal element 52 located in the lower portion of gap 26 as indicated in FIG. 1. Thermal element 52 is located so as to deliver thermal energy to the user's sacroiliac at the base of the user's spine.

Body-facing side 28 of flexible web 12 contains foamed polymer strips 38 aligned transverse to longitudinal axis 18 of web 12 for increasing friction between back wrap 10 and the wearer's body. This increased friction serves to reduce the slippage or relative movement between back wrap 10 and the wearer. Preferably, foamed polymer strips 38 may also be made visually different (e.g. color) from web 12. Visual differentiation can be used by the user as an alignment aid during application of wrap 10 to provide proper positioning of gap 26 over the spine of the user's body. Alternatively, a high-tack polymer, such as Ethyl Vinyl Acetate (EVA), may be used instead of foamed polymer strips to provide the high friction and/or visual alignment guide. Strips 38 may be glued, thermally bonded, or printed onto body facing side 28.

Preferably, flexible web 12 has a first fibrous layer 60 at outer surface 30, a second fibrous layer 62 at body-facing side 28, and an elastic member 64 interposed therebetween. Fibrous layer 60 and fibrous layer 62 may be a number of different materials which include but are not limited to: woven or knit fabrics that have been brushed to increase the "nap" and expose more "loops", through-air bonded nonwovens, carded nonwovens, spunbonded nonwovens, etc.

Elastic member 64 can be selected from natural or synthetic rubber, or any number of polymeric materials which are capable of elongation and recovery. Suitable materials include but are not limited to: Styrene Block Copolymers; rubber, and Lycra™, a trademark of E. I. DuPont De Nemours of Wilmington, Del., and Krayton™, a trademark of Shell Oil Co. of Houston, Tex. They may also include: polyethylenes including metallocene catalyst PE; foams, including polyurethane and polyester, etc. Elastic member 64 can be in the form of: strands, scrims, ribbons, tapes, structural elastic-like films.

Elastic member 64 can be bonded to fibrous layer 60 and 62 in any number of ways including but not limited to: double sided adhesive tapes, hot melt adhesive, pressure sensitive adhesives, ultrasonic bonding, pressure bonding, etc. Adhesives, if used, can be applied via hot melt beads, foam, spiral hot melt, melt blown, spray, immersion, transfer, etc. Suitable elastic properties can be achieved via a number of construction techniques: lamination with strained elastic, zero-strain elastics with subsequent activation in either machine direction or cross direction, or a combination of these techniques.

A preferred method of construction of flexible web 12 is accomplished by first straining elastic member 64 in the longitudinal direction at least thirty percent. That is, the dimension in the longitudinal direction of web 12 when it is strained is at least thirty percent longer than the unstrained dimension of web 12. While elastic member 64 is held in this strained configuration, fibrous layer 60 and fibrous layer 62 ate juxtaposed on either side of elastic member 64 and discontinuously bonded one to another at bond sites 66. Once bonded, elastic member 64 is allowed to relax and return to its unstrained configuration. This relaxing of elastic member 64 causes fibrous layers 60 and 62 to pucker and form rugosities 68 between bond sites 66. Rugosities 68 of fibrous layer 60 provide a plurality of loop fibers 32 on outer surface 30. Ideally, elastic member 64 is strained sufficiently during assembly of web 12 such that during normal use the wearer does not fully extend web 12. If web 12 were fully extended, during use, to the dimension at which it is constructed, the amplitude of rugosities 68 would be minimized, lowering the engagement force between hooks 34 and loop fibers 32.

In a particularly preferred embodiment of the present invention wrap 10 is made using the following materials and method. A film of Styrene Block Copolymer (SBC) is bonded to two layers of polypropylene (PP) spunbond nonwoven. A trilaminate is made by stretching the elastic SBC about 100% (twice its original length). While the SBC is held in this strained position, a layer of PP nonwoven is positioned on either side. The trilaminate is ultrasonically bonded together in a discrete pattern of bond sites 66, spaced about 8 mm apart along longitudinal axis 18. The trilaminate is then released and allowed to return to a relaxed position. The PP nonwoven is gathered or puckered between the bonding sites. An SBC that has been successfully used is a 0.0024 inch (2.4 mil) thick EXX500D which is produced by Exxon Chemicals of Lake Zurich, Ill. Nonwovens that have been successfully used are a 14 gram/square yard (gsy) and a 17 gsy spunbond PP available from Veratec of Walpole, Mass. The combining operation (stretching, combining, bonding) has been clone by Veratec of Walpole, Mass. The resulting trilaminate elastic material is available from Veratec as PO671.0.

Hook member 36 and loop fibers 32 ideally are chosen to provide shear strength greater than the elastic tension exerted by wrap 10 during use. Hook member 36, found to work particularly well with the above described elastic loop material, comprises harpoon shaped hooks 34, which are oriented parallel to longitudinal axis 18 of web 12. Such hooks are available from Aplix of Charlotte, N.C., and are available as 960B. Hooks 34 are permanently mounted to grip tab 40 by means of adhesive, ultrasonic bonding, pressure bonding, or stitching. Grip tab 40 is then attached to first end 14 of wrap 12 by adhesive.

Thermal elements 22 are preferably heating elements, which are described in a copending application entitled "A HEAT CELL", filed on the same day as the present application via U.S. Express Mail EG088459522US, and obligated to be assigned to the assignee of the present application, which is hereby incorporated by reference. A preferred heat cell comprises from about 30% to about 80% iron powder; from about 3% to about 25% activated carbon, non-activated carbon, and mixtures thereof; from about 0.5% to about 10% metal salt; and from about 1% to about 40% water; wherein the particles of the particulate exothermic composition are combined in a cell, formed in a unified structure comprising at least two opposed surfaces, wherein at least one surface is oxygen permeable, that when filled with said particulate exothermic composition, has a fill volume and a cell volume whereby the ratio of fill volume to cell volume is from about 0.7 to about 1.0, wherein the ratio is maintained without the use of differential pressure across the cell wall. All percentages and ratios used herein are by weight of the total composition, and all measurements are made at 25° C., unless otherwise specified. Thermal elements 22 are constructed by thermoforming base material 70 to form a pocket 76. Pocket 76 in base material 70 is then filled with chemistry 74. After filling pocket 76 in base material 70 with chemistry 74, cover material 72 is placed over pocket 76 and heat sealed to base material 70 around the periphery of pocket 76, encapsulating chemistry 74. Small holes are then pierced in base material 70 and/or cover material 72 to allow oxygen to reach chemistry 74.

Base material 70 and cover material 72 may be made of any number of materials capable of containing chemistry 74 and limiting oxygen flow into pocket 76. Materials that have been used successfuly are 42 gram per square meter polypropylene spunbond nonwoven which have been extrusion coated with low density polyethylene and/or ethyl vinyl acetate (EVA) at a thickness of 50 to 75 microns. Thermal elements 22 are preferrable about 25 mm in diameter and about 6 mm in height.

Chemistry 74 is preferably a mixture of powdered iron, powdered activated charcoal, vermiculite, water, and salt. Mixtures of this type react when exposed to oxygen providing heat for several hours. Prior to use, wrap 10 with thermal elements 22 is enclosed within an oxygen impermeable package. To use, wrap 10 is removed from the oxygen impermeable package allowing oxygen to enter pockets 76 and react with chemistry 74 of thermal elements 22.

Thermal elements 22 are arranged on wrap 10 in diamond-shaped pattern 24. The dimensions of pattern 24 are about 225 mm to about 300 mm measured in a direction parallel to transverse axis 18 and about 115 mm to about 200 mm measured in a direction transverse to longitudinal axis 18.

Using the materials described above for construction of wrap 10, most people can be accommodated with only two different sizes of wrap 10. The smaller size of wrap 10 has a dimension of about 915 mm measured in a direction parallel to the longitudinal axis 18 when wrap 10 is in a relaxed or untensioned state and a dimension of about 125 mm to about 150 mm measured in a direction transverse to the longitudinal axis 18. The larger size of wrap 10 has a dimension of about 1100 mm measured in a direction parallel to the longitudinal axis 18 when wrap 10 is in a relaxed or untensioned state and a dimension of about 135 mm to about 150 mm measured in a direction transverse to the longitudinal axis 18. These two sizes of wrap 10 will accommodate most peolpe with waist sizes of less than about 1220 mm.

Four anti-slip foam strips 38 are preferrably positioned symetrically on either side of diamond-shaped pattern 24. Preferrably two foam strips 38 are postioned adjacent diamond-shaped pattern 24, one on either side as depicted in FIG. 1. Two additional foam strips 38 are equally spaced about 125 mm to about 175 mm distance, as measured parallel to longitudinal axis 18, from diamond-shaped pattern 24 as depicted in FIG. 1. A fifth foam strip 38 is positioned adjacent second end 16 as depicted in FIG. 1. Anti-slip foam strips 38 are preferrably about 25 mm wide and about 1.5 mm thick.

Further details concerning the back wrap of the present invention may be found in copending application entitled "ELASTIC WRAP HAVING NON-TARGETED RECLOSABLE FASTENER", filed on the same day as the present application via U.S. Express Mail EF280762640US, and obligated to be assigned to the assignee of the present application, which is hereby incorporated by reference.

While particular embodiments of the present invention have been illustrated and described, it will be obvious to those skilled in the art that various changes and modifications may be made without departing from the spirit and scope of the invention, and it is intended to cover in the appended claims all such modifications that are within the scope of the invention.

What is claimed is:

1. A disposable elastic back wrap comprising:

a) a substantially rectangular piece of flexible web having a first end and a second end and an elastic portion therebetween stretchable along a longitudinal axis of said piece of flexible web, said piece of flexible web having a length great enough to encircle a user's waist such that said first and second ends overlap, said first end having a reclosable fastening system for attaching said first end to said piece of flexible web near said second end in order to hold said piece of flexible web around said user's waist when said piece of flexible web is stretched, said fastening system having a plurality of hook members which engage loop fibers of said piece of flexible web anywhere along said piece of flexible web in order to adjust said wrap to a variety of user waist sizes and to attain a comfortable level of elastic tension;

b) a plurality of individual heat generating thermal elements encapsulated within said piece of web, said plurality of the thermal elements having an oxygen activated chemistry and a substantially planar diamond-shaped pattern which approximates the shape of erector muscles in the user's back; and c) a means for increasing friction between said piece of flexible web and a user's body in order to reduce slippage of said back wrap during use.

* * * * *